(12) United States Patent
Azuma

(10) Patent No.: US 8,506,483 B2
(45) Date of Patent: Aug. 13, 2013

(54) ULTRASONOGRAPHIC DEVICE

(75) Inventor: Takashi Azuma, Kodaira (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 549 days.

(21) Appl. No.: 12/374,065

(22) PCT Filed: Jun. 14, 2007

(86) PCT No.: PCT/JP2007/062021
§ 371 (c)(1),
(2), (4) Date: Sep. 29, 2009

(87) PCT Pub. No.: WO2008/010366
PCT Pub. Date: Jan. 24, 2008

(65) Prior Publication Data
US 2010/0049042 A1 Feb. 25, 2010

(30) Foreign Application Priority Data

Jul. 18, 2006 (JP) .................. 2006-195674

(51) Int. Cl.
*A61B 8/00* (2006.01)

(52) U.S. Cl.
USPC .................... 600/437; 600/443; 600/455

(58) Field of Classification Search
None
See application file for complete search history.

(56) References Cited

U.S. PATENT DOCUMENTS

| 4,787,252 A * | 11/1988 | Jacobson et al. .......... 73/861.28 |
| 4,930,514 A * | 6/1990 | Baba et al. .................... 600/455 |
| 2001/0034485 A1 | 10/2001 | Kawagishi et al. |
| 2005/0018133 A1 * | 1/2005 | Huang et al. ................. 351/205 |

FOREIGN PATENT DOCUMENTS

| JP | 05-154153 | 6/1993 |
| JP | 07-095978 | 4/1995 |
| JP | 11-009603 | 1/1999 |
| JP | 11-276477 | 10/1999 |
| JP | 2001-286472 | 10/2001 |
| JP | 2005-087266 | 4/2005 |

* cited by examiner

*Primary Examiner* — Long V. Le
*Assistant Examiner* — Bo J Peng
(74) *Attorney, Agent, or Firm* — Antonelli, Terry, Stout & Kraus, LLP.

(57) ABSTRACT

It possible to provide an ultrasonogram having a preferable spatial resolution and signal/noise ratio. A signal dynamic range is measured so that selection between a linear interpolation or sinc function interpolation is adaptively performed for the signal or weighted averaging of the both is performed. It is possible to set in advance a depth position for switching between the linear interpolation and the sinc function interpolation in a storage unit (21) so that the two interpolation methods are switched from one to the other at the boundary of the depth position.

11 Claims, 17 Drawing Sheets

(a)

(b)

(a)

(b)

Weighting function (a)

(b)

(a) Histogram of difference of intensity (b) Weighting function W

ULTRASONOGRAPHIC DEVICE

TECHNICAL FIELD

The present invention relates to a device that displays an ultrasonogram.

BACKGROUND ART

Heretofore, a beam scanning method of emitting a beam from a small-diameter aperture to scan a sectoral region for acquiring a broad field of view has been widely employed in ultrasonography. Examples of the method include so-called sector scan and so-called convex scan. A broader field of view is more advantageous to find a lesion. However, it is also true that a smaller aperture diameter may be more advantageous in some cases as follows. Specifically, the smaller surface area a probe has, the more advantageous it is in such cases as where an area available for the probe contact is limited in a subject to be examined. Examples of such cases include where the probe needs to be pressed against a narrow area between ribs such as in imaging a heart. However, if a surface area of a probe is reduced, the number of rasters obtained therewith is also reduced. If scan conversion is performed on data with a reduced number of rasters so as to display the data on a video display, the resultant image will be degraded. Patent Document 1 discloses a method for preventing such image degradation. In this method, a received signal is converted into a complex signal, and a real part and an imaginary part of the complex signal are individually interpolated by using sinc functions.

[Patent Document 1] JP-A 11-9603

DISCLOSURE OF THE INVENTION

Problem to be Solved by the Invention

However, a larger number of rasters are used to compute a single interpolated data point in interpolation using sinc functions than in simple linear interpolation. Accordingly, if data on a certain raster includes noise, sinc function interpolation expands an effect of the noise to distant points. Thus, sinc function interpolation is not necessarily optimal for data containing noise, so that a challenging issue of deciding whether to apply sinc function interpolation to a certain processing-target data remains unsolved.

An object of the present invention is to provide an ultrasonographic device capable of applying optimal interpolation to processing-target data to contribute to reduction of noise contained in rasters.

Means for Solving the Problem

According to the present invention, a signal dynamic range for each acquired signal is measured to determine a point either for adaptively switching between linear interpolation and sinc function interpolation or for employing a weighted average of interpolated values respectively obtained by these interpolation methods. The depth point for switching between linear interpolation and sinc function interpolation may be previously stored in a certain unit, and an interpolation method for use may be switched between these two methods at the interpolation method transition depth. Instead of completely switching between these two methods at the interpolation method transition depth, a weighted sum of interpolated values respectively obtained by the two interpolation methods may be used as an interpolated value.

DESCRIPTION OF SYMBOLS

| | |
|---|---|
| 1 | ultrasonic probe |
| 2 | transmit/receive switch |
| 3 | transmission beam former |
| 4 | controller |
| 20 | receiving beam former |
| 21 | depth storage unit |
| 22 | interpolation method setting unit |
| 23 | scan converter |
| 24 | display |
| 29 | memory |
| 30 | interpolation processor |
| 31 | noise reduction filter |
| 32 | diagnostic system main unit |
| 33 | interface of transition point control |
| 101 | parameters set process |
| 102 | weighting value computing area setting process |
| 103 | weighting value computing process |
| 104 | completion decision process |
| 105 | intensity adjustment process |
| 106 | decision process |

BEST MODES FOR CARRYING OUT THE INVENTION

Hereinafter, embodiments of the present invention will be described with reference to the drawings.

Figure 1:
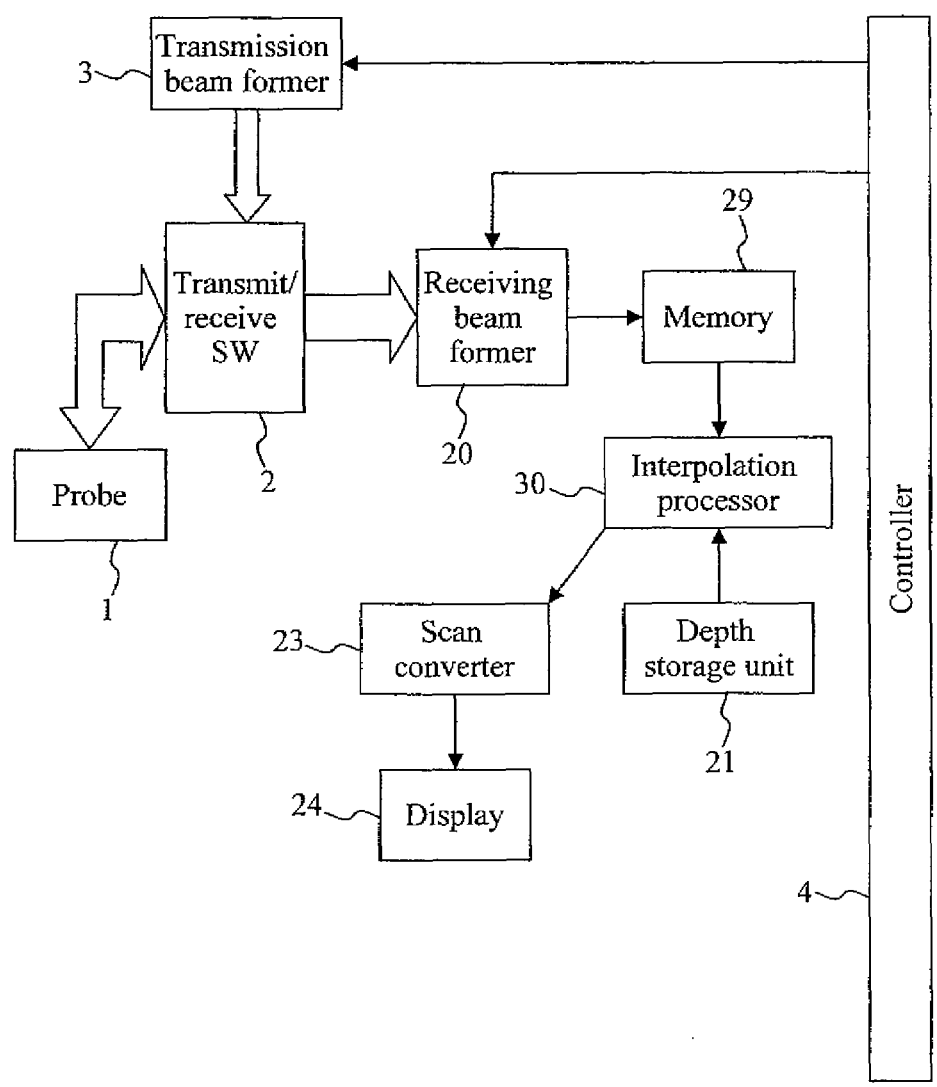
FIG. 1 is a functional block diagram illustrating an example of an ultrasonographic device according to the present invention.

FIG. 1 is a functional block diagram illustrating an example of an ultrasonographic device according to the present invention. Firstly, description will be given of a flow of signal processing for imaging in the ultrasonographic device. A transmission beam former 3 controlled by a controller 4 transmits transmission electrical pulses via a transmit/receive switch 2 to an ultrasonic probe 1 that is placed on the surface of a subject to be examined. In this event, the transmission beam former is controlled such that delay times among channels of the probe 1 can be adjusted to cause each ultrasonic beam to travel along a desired raster. Then, the ultrasonic probe 1 converts each electrical signal transmitted from the transmission beam former 3 into an ultrasonic signal, and transmits, as an ultrasonic pulse, the signal into the subject to be examined. The ultrasonic pulse scattered in the subject to be examined is partly transmitted back to and received by the ultrasonic probe 1 as an echo signal. Then, the ultrasonic probe 1 converts the echo signal into an electrical signal. The received signals are transmitted to a receiving beam former 20 via the transmit/receive switch 2, and then stored in a memory 29 as data obtained by selectively amplifying the echo signals transmitted from a desired depth along the desired rasters. An interpolation processor 30 interpolates data between each adjacent two rasters from which actual data is obtained, and thereby increases the number of rasters. In this event, the interpolation processor 30 selects the optimal interpolation method from the multiple methods as will be described later. The interpolated data is transmitted to the scan converter 23, which performs scan conversion on the data. The data after scan conversion is transmitted to a display unit 24, which displays the data as an ultrasonogram.

Figure 2:
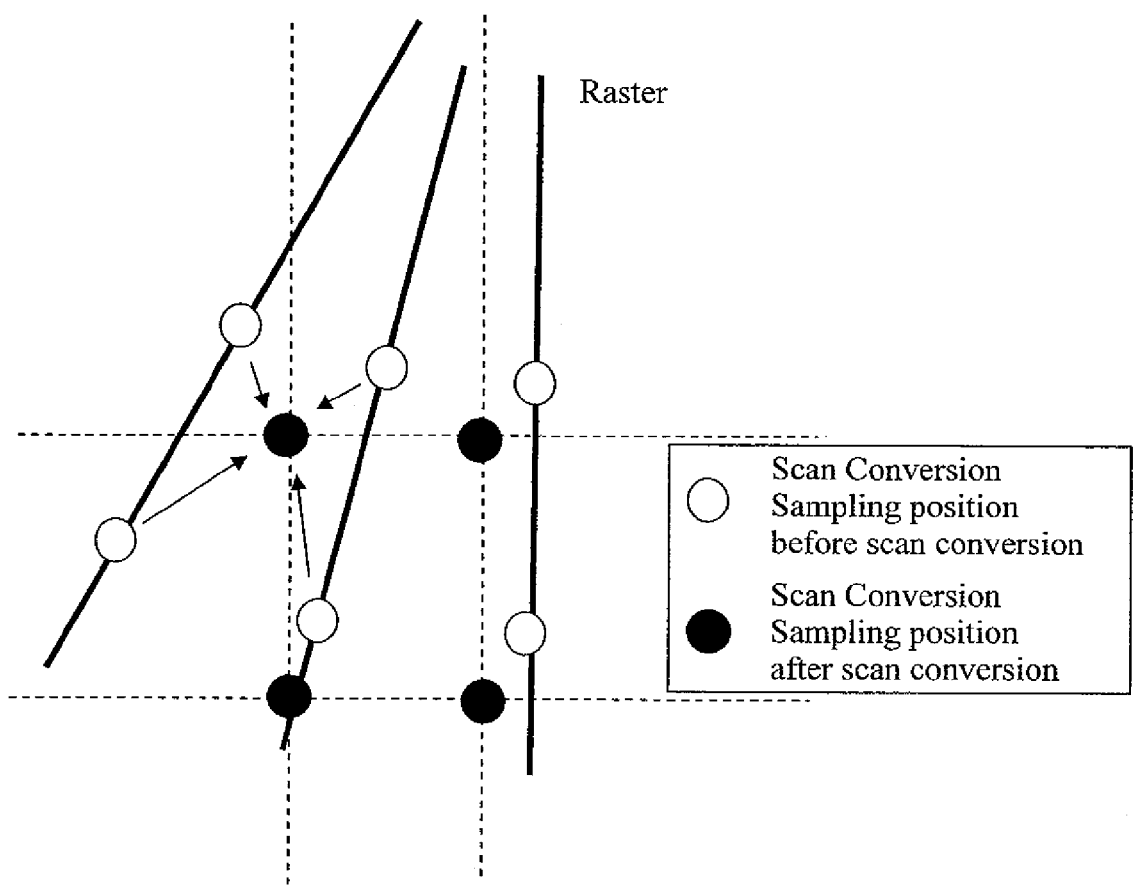
FIG. 2 illustrates a mechanism of scan conversion.

Hereinbelow, interpolation and scan conversion according to the present invention will be described. Firstly, with reference to FIG. 2, description will be given of a scan conversion method from echo data obtained by sector scanning or convex scanning into video image data expressed in an orthogonal coordinate system. In scan conversion, an intensity value at each data point (black circle in FIG. 2) after scan conversion is computed from intensity values of multiple data points (white circles in FIG. 2) before scan conversion surrounding the data point after scan conversion. In this event, no careful attention needs to be paid to what scan conversion method to employ if spatial sampling intervals in data after scan conversion are sufficiently wider than those in data before scan conversion. However, if spatial sampling intervals in data after scan conversion are not sufficiently wider than those in data before scan conversion, an output image is strongly affected by what scan conversion method to employ. Here, suppose that scan conversion is performed in two stages: (1) sufficiently narrowing down sampling intervals in data before scan conversion by using interpolation; and (2) performing scan conversion on the data. Then, the above consideration on what scan conversion method to employ is boiled down to consideration on what interpolation method to employ.

To obtain an ultrasonic image, each of transmission and received beams is focused. However, beam focusing in the horizontal direction is limited by the diffraction effect. In addition, rasters are typically arranged side by side in the horizontal direction at intervals each having a length from a half to a quarter of a wavelength at the center frequency at the corresponding position. This is because too dense arrangement of rasters in the horizontal direction will lead to decrease in frame rate. Consequently, each sampling interval in the horizontal direction is around from 125 µm to 250 µm if, for example, the center frequency is 3 MHz. On the other hand, in the depth direction, sufficiently dense sampling with respect to the frequency of the carrier is performed. Accordingly, each sampling interval in the depth direction is computed to be around from 20 µm to 25 µm if it is assumed that an A/D converter normally performs sampling at 30 MHz to 40 MHz, and that the sound speed is 1500 m/s. As has been described, sampling density in the azimuth direction is much lower than in the depth direction, and thus interpolation in a two-dimensional scan conversion can be dealt with as a matter of one-dimensional interpolation in the azimuth direction.

Figure 3:
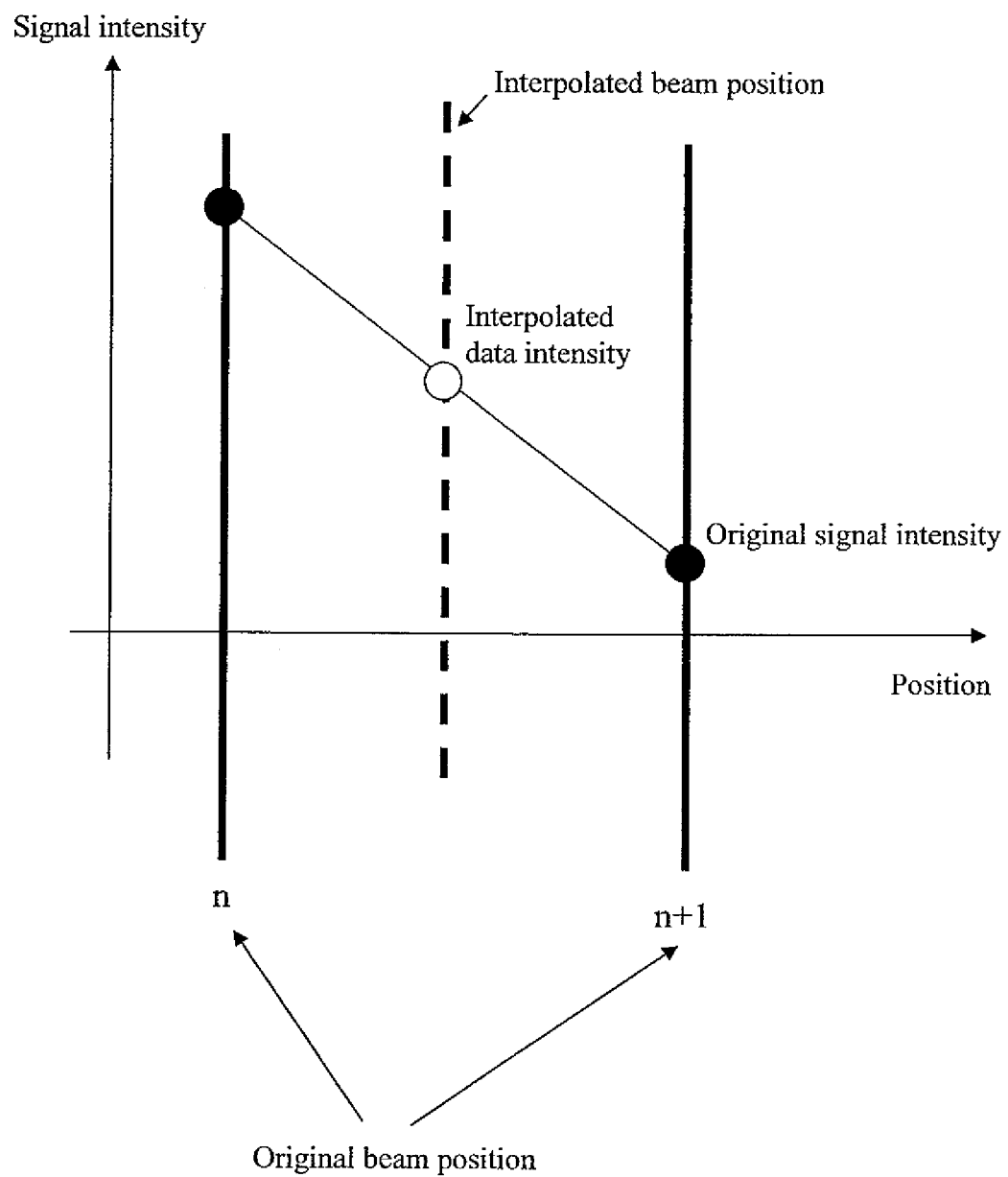
FIG. 3 is a graph for illustrating linear interpolation.
Figure 4:
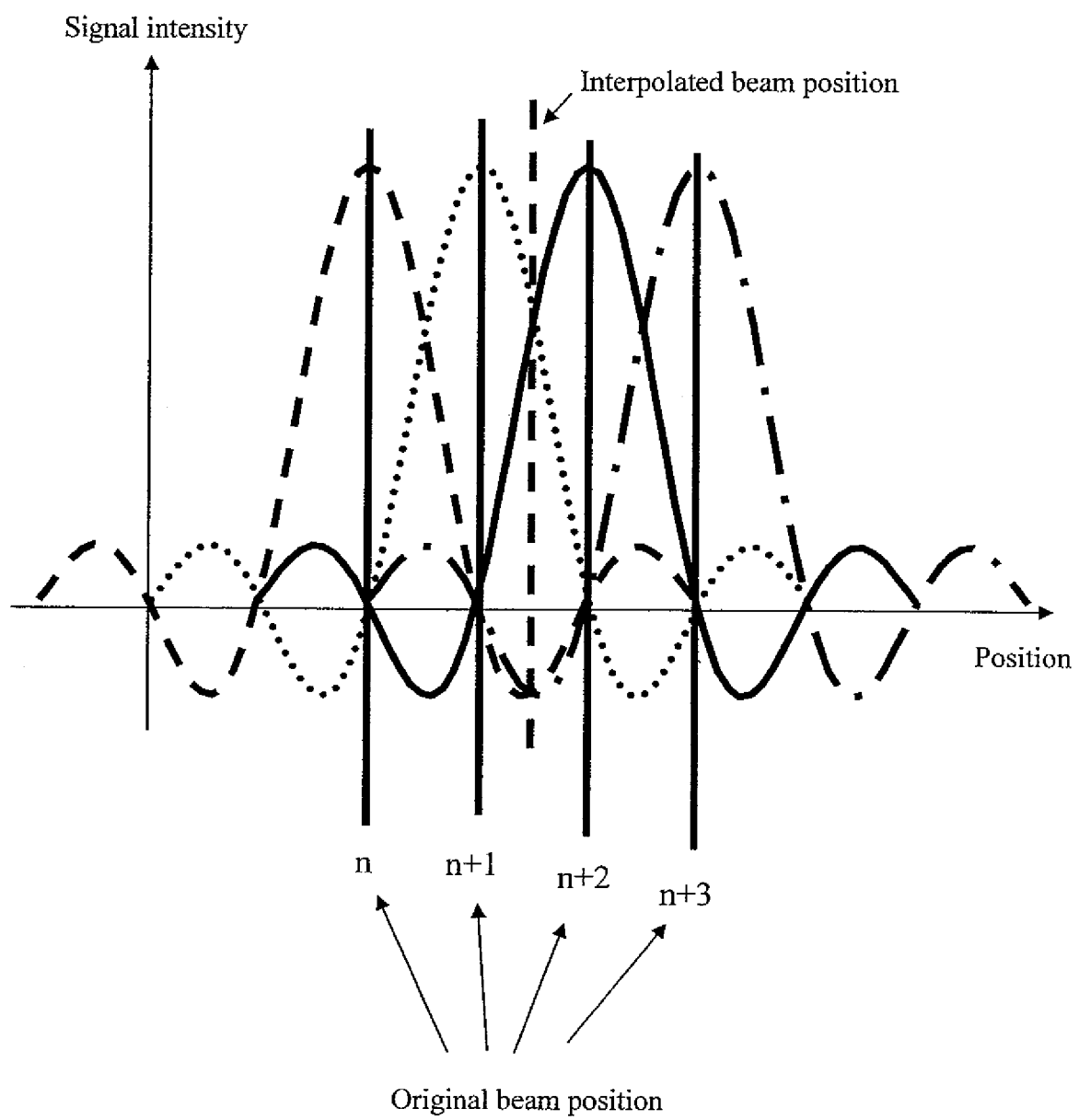
FIG. 4 is a graph for illustrating sinc function interpolation.

As one-dimensional interpolation methods, interpolation methods shown in FIGS. 3 and 4 are usually employed. FIG. 3 is a graph for illustrating linear interpolation. In linear interpolation, an intensity value of each data point after interpolation is obtained through interpolation between intensity values of two closest points respectively positioned at both sides of the data point to be obtained after interpolation. Meanwhile, FIG. 4 is a graph for illustrating sinc function interpolation using four or more data points. In sinc function interpolation, each data point is supposed to be a representative point in a space having a finite width, and an interpolation coefficient is determined using a sinc function obtained as a Fourier transform of a rectangular function representing the finite width. As an intensity value of interpolated data at a position indicated by the dashed line in FIG. 4, an interpolated value is obtained by adding up the following values: values obtained by multiplying intensity values of pixels adjacent to the position by a coefficient of $2/\pi$; and values obtained by multiplying intensity values of pixels outwardly adjacent to these respective pixels by a coefficient of $-3/2\pi$. Here, the coefficient of $2/\pi$ is obtained from sinc functions (indicated by the solid line and the dotted line in FIG. 4) that reach their peaks at the aforementioned adjacent pixels, respectively. Meanwhile, the coefficient of $-3/2\pi$ is obtained from sinc functions (indicated by the dashed line and the alternate long and short dash line in FIG. 4) that reach their peaks at the aforementioned pixels outwardly adjacent to these adjacent pixels, respectively.

It is known that use of these interpolation methods deliver substantially the same outcome, if interpolation-target data has a sufficiently higher sampling frequency than its data frequency, but that use of interpolation using sinc functions delivers more accurate outcome, if interpolation-target data does not have a sufficiently higher sampling frequency than its data frequency. If an interpolated position is fixed, interpolation coefficients (such as $2/\pi$ and $-3/2\pi$ described above) previously computed using sinc functions can be employed. Accordingly, no computational load attributable to use of sinc functions is generated. However, if the interpolated position is variable, it is necessary to compute interpolation coefficients for each interpolated position by using sinc functions, which generates much computational load. For practical purposes, such calculation does not necessarily require use of sinc functions, though. Instead, each sinc function may be approximated by Taylor expansion and then truncated to the finite number of terms, and the above calculation may be performed using the approximative functions thus obtained. Even this approach will present no practical problem. In particular, truncating each sinc function to the finite number of terms is rather preferable since this interpolation processing needs to be performed at a speed higher than a frame rate of the ultrasonographic device on a DSP, in practical terms. In this case, when a sinc function is approximated by Taylor expansion about a point a and truncated to terms up to the third-order, the following is obtained:

Sin(a)/a+(x−a)(cos(a)/a−sin(a)/a²)+(x−a)²/2x(−sin(a)/a−2 cos(a)/a²+2 cos(a)/a³)+(x−a)³/6x(−cos(a)/a+3 sin(a)/a²+4 cos(a)/a³−2 sin(a)/a³−6 cos(a)/a⁴).

Accordingly, when expanded about a point of π/2 in the same manner, the sinc function can be approximated by the following at most third-order polynomial:

$$(2/\pi^2-8/3\pi^3)x^3+(4/\pi^2-4/\pi)x^2+(-4/\pi^2-2/\pi+5/2)x+(4/\pi-\pi/2+1/3).$$

The center value for expansion should preferably vary in accordance with an interpolated position, such as one set in interpolation from adjacent points, or in interpolation from points two points from the interpolated position. This can reduce necessary orders for the expansion coefficient.

An ultrasonic image is a convolution of a point spread function specific to imaging conditions of a device, and a scatterer distribution in a subject. Here, the imaging conditions are determined by beam forming and post processing. In the current ultrasonography, transmission beam forming and receiving beam forming are individually performed, and only a single point is focused on and thus the other points are focused off in each raster in the transmission beam forming. This is because, in the transmission beam forming, prevention of frame rate decrease is considered as a higher-priority issue than achievement of uniform focus. On the other hand, a configuration allowing a so-called dynamic focus in the receiving beam forming has been implemented. In the dynamic focus, focus points are continuously transitioned in accordance with receiving timings so that each raster image is uniformly focused on in the depth direction.

Figure 5:
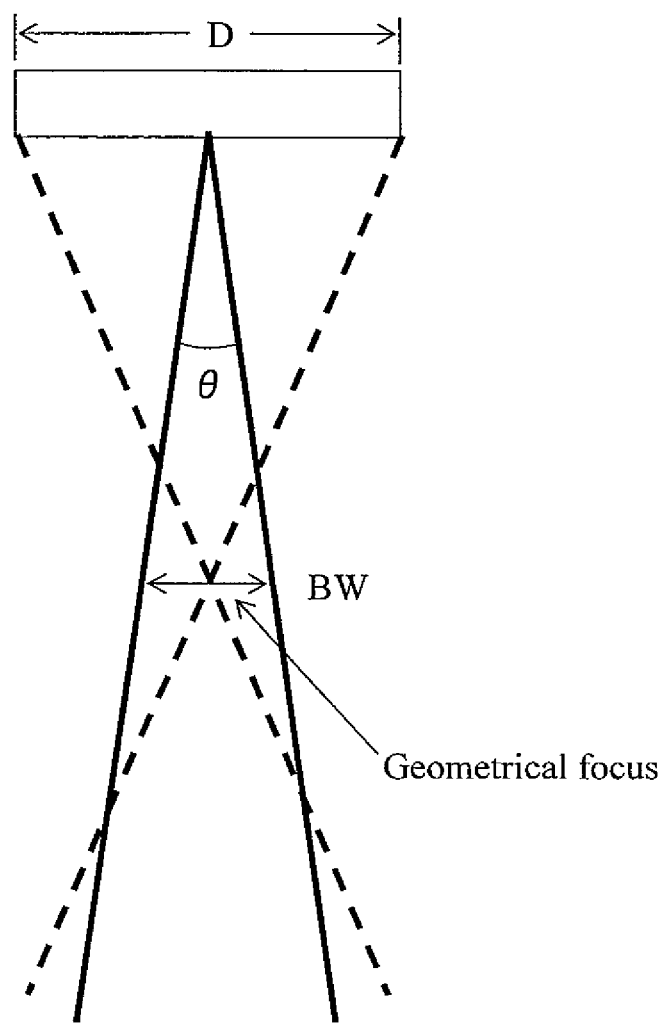
FIG. 5 illustrates a beam width.

A critical lateral blurring might occur in an echo from a deep part of a living body, and a spread of a point spread function, that is, an azimuth resolution, in such a deep part depends on a receiving beam width. A beam width BW at a focus point depends on diffraction effect of ultrasonic waves rather than on the geometrical beam width, as shown in FIG. 5. A diffraction angle θ can be approximated by the following equation. Here, λ is a wavelength, and D is an aperture diameter width.

$$\theta=\sin^{-1}(\lambda/D)$$

A beam width will be computed by using a typical example below. Assume that a center frequency in a deep part is 2 MHz, an aperture diameter width of 12.5 mm, and a distance from a probe surface to an imaging-target site is Z. Here, the aperture diameter width is obtained by approximating a transmission aperture diameter weighting value at a half. Then, the diffraction angle is 0.06 rad, and thus the beam width is 0.06×Z mm. Meanwhile, a typical raster width is on the order of 0.01×Z mm. This means that a sampling interval is approximately six times narrower than the beam width, and thus linear interpolation will be good enough in typical cases.

Figure 6:
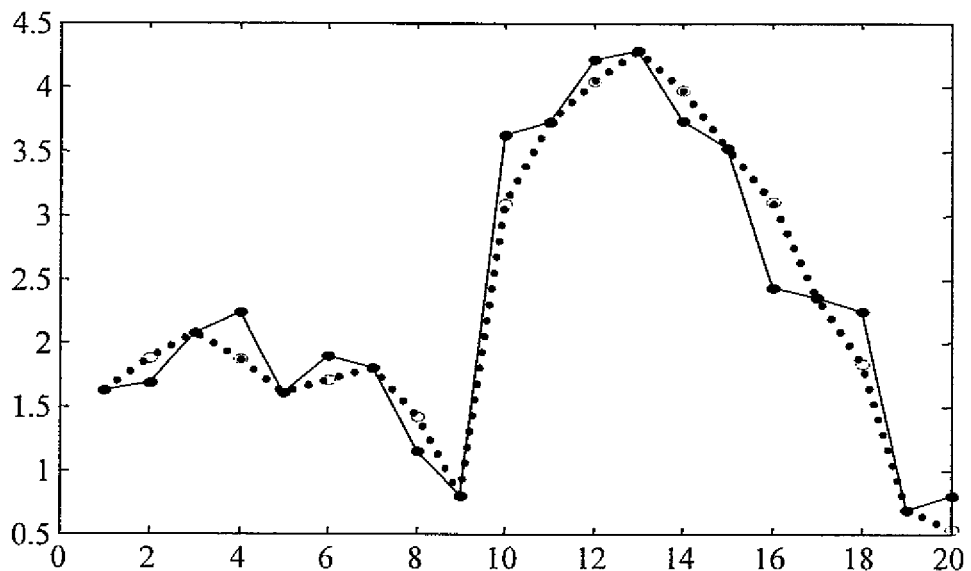
FIG. 6 shows examples of experimental data indicating interpolation results.
Figure 6:
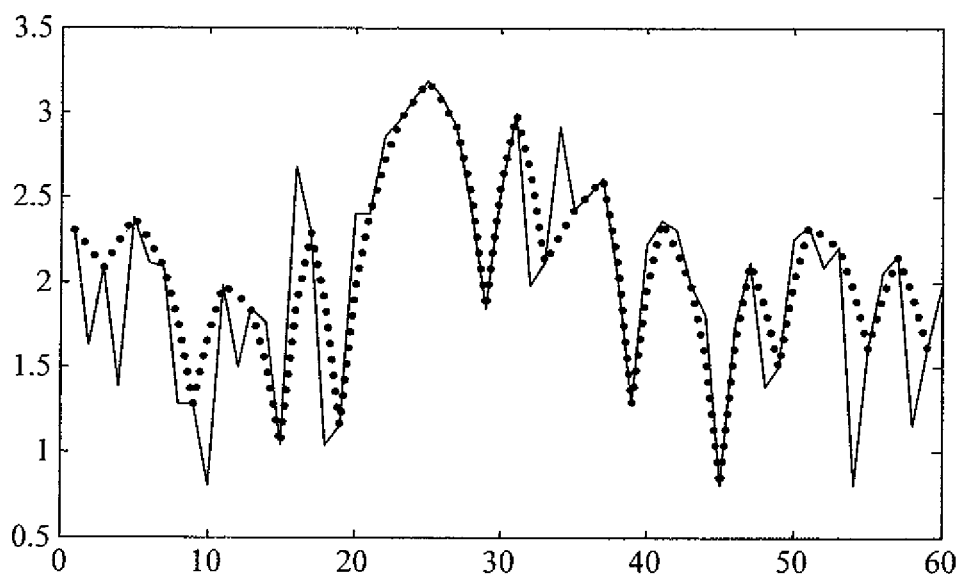

FIG. 6 shows experimental results. In each graph, the vertical axis indicates intensity while the horizontal axis indicates a horizontal position. In FIG. 6(a), which shows data on echo signals from point reflectors, the black circles connected by the solid line correspond to data points sampled by double density scanning while the white circles connected by the dotted line correspond to data points obtained by firstly sampling data by normal scanning and then doubling the density of the sampled data by linear interpolation. There is little difference in these two experimental results, and thus these lines overlap each other in most parts. This indicates that the linear interpolation causes substantially no image degradation in this case. The result matches what is estimated to occur in the case where a beam width is sufficiently greater than a raster width as described above.

Meanwhile, in FIG. 6(b), which shows data on speckle signals, the solid line corresponds to data points sampled by double density scanning while the dotted line corresponds to data points obtained by firstly sampling data by normal scanning and then doubling the density of the sampled data by linear interpolation. As is clear from FIG. 6(b), signals with high spatial frequency components are lost in the experimental result obtained by linear interpolation. As a result, a cross-sectional image obtained by linear interpolation will give an impression of suffering from a lateral blurring.

Figure 7:
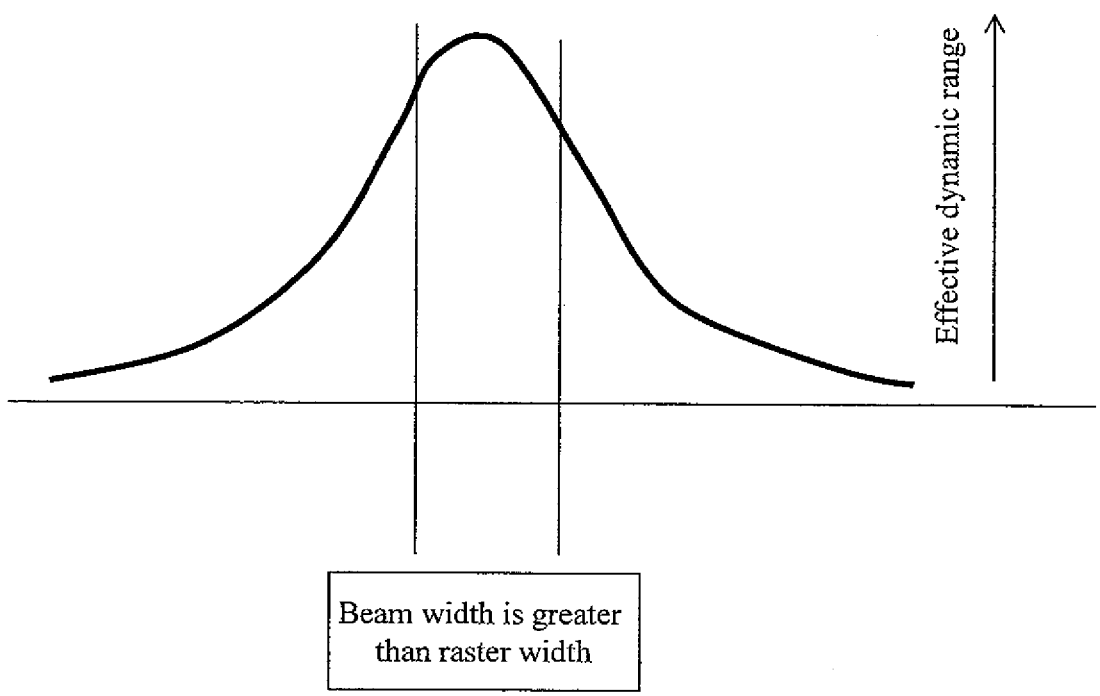
FIG. 7 is a graph for illustrating a relation between a signal dynamic range and a beam width.
Figure 8:
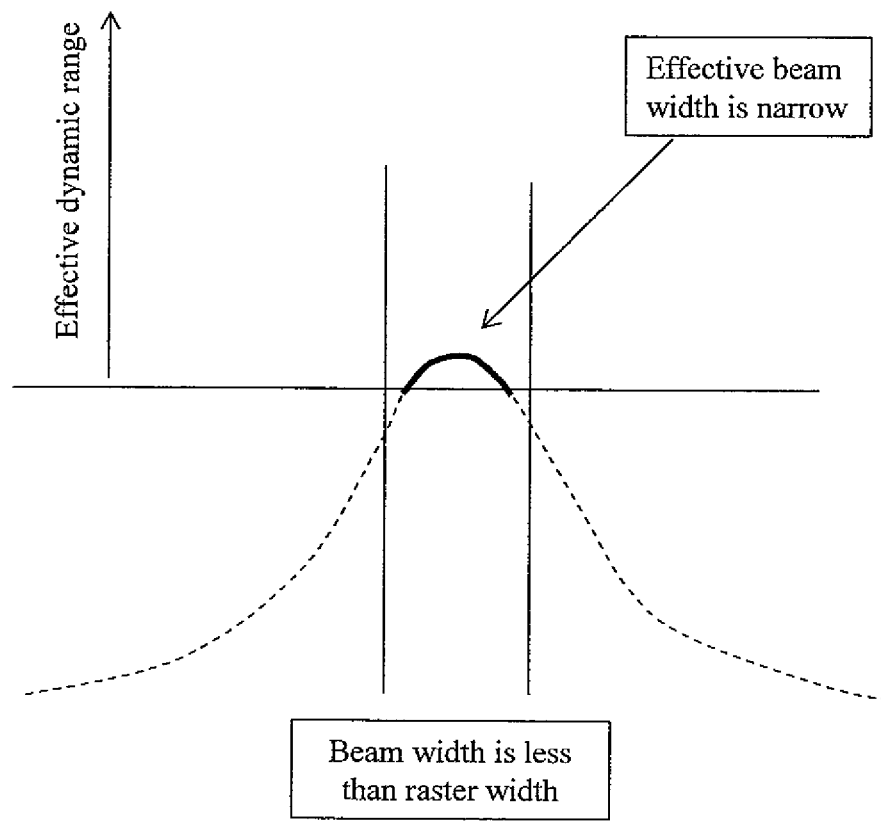
FIG. 8 is a graph for illustrating a relation between a signal dynamic range and a beam width.

Firstly, review will be made on what causes the result different from the initial estimation, that is, the result that linear interpolation on speckle signals caused some lateral blurring while sinc function interpolation on speckle signals caused no lateral blurring. This result is explainable by the fact that a signal dynamic range is limited. Specifically, the existing ultrasonographic device has a limited dynamic range, such as 150 dB of an A/D converter. Accordingly, if a scatterer has high reflection intensity, a beam width is equal to the spatial width of the reflected signal as shown in FIG. 7. However, suppose the case where a reflected signal has relatively low reflection intensity such as a speckle signal, and is reduced in signal intensity such as an echo signal from a deep part since an ultrasonic beam is attenuated while propagating in a living body. In this case, the signal has a narrow width in the effective dynamic range as shown in FIG. 8. As described above, in such a case as shown in FIG. 8, it is necessary to employ, as an interpolation method, sinc function interpolation rather than linear interpolation.

Figure 9:
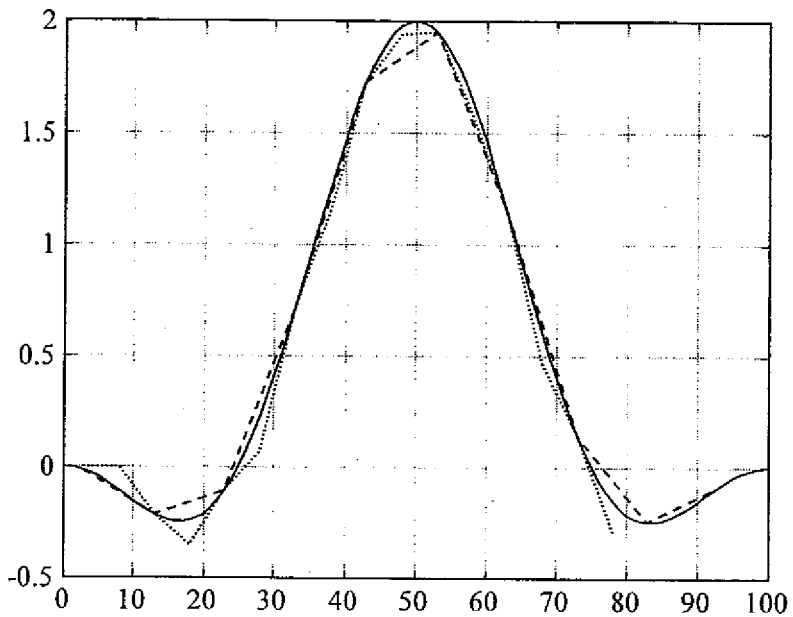
FIG. 9 illustrates that an effect of noise varies depending on what interpolation method is employed.
Figure 9:
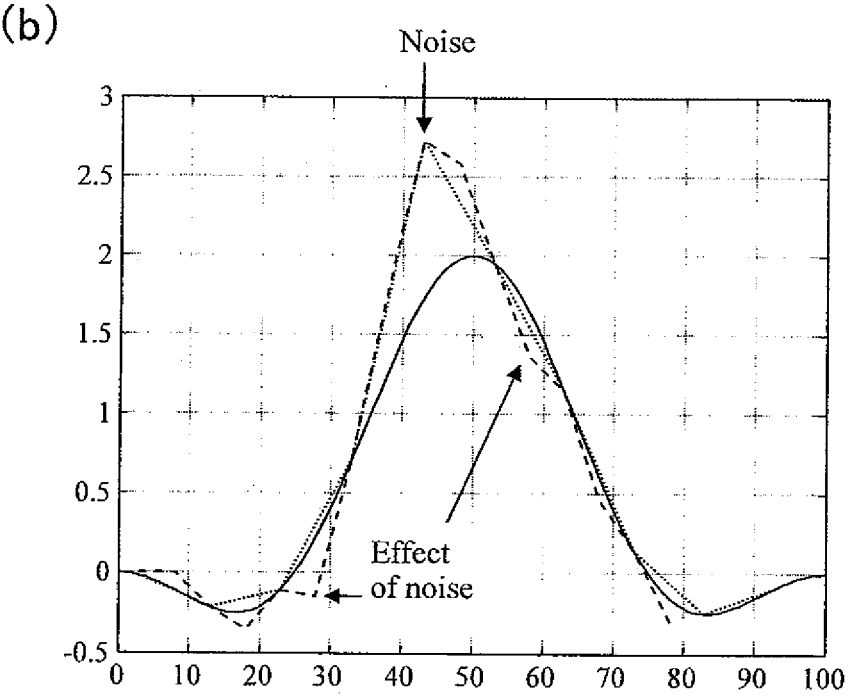

FIG. 9 shows principle experiment results of evaluating an effect of noise on data after interpolation. Here, evaluation is made by approximating an ideal beam before noise addition by a sinc function, and using virtual data with noise obtained by adding noise like a delta function to the approximated function. In FIG. 9(a), which shows data without noise, the solid line, the dotted line and the dashed line indicate ideal beam data, linear-interpolated data and sinc-function-interpolated data, respectively. If original data contains no noise, the sinc-function-interpolated data comes closer to the original data than the linear-interpolated data. FIG. 9(b) shows a result obtained by adding noise at the position indicated by the arrow in the FIG. 9(b). As is clear from FIG. 9(b), a range where an effect of noise is present is different between the sinc-function-interpolated data and the linear-interpolated data. Specifically, if linear interpolation is used for data including some noise, the range where the effect of the noise is present in the interpolated data is limited to interpolated points adjacent to the position containing the noise. By contrast, if sinc function interpolation is used for data containing some noise, the effect of the noise reaches not only interpolated points adjacent to the position containing the noise but also interpolated points adjacent to these adjacent points.

In Table 1, results of simulation evaluation on effect of the interpolation method on noise are summarized. In the evaluation, 20 log (error in sinc function interpolation/error in linear interpolation) was computed. In Table 1, each positive dB value indicates that linear interpolation is more preferable while each negative dB value indicates that sinc function interpolation is more preferable.

TABLE 1

| S/N | sampling | | |
|---|---|---|---|
| | $\lambda/2.5$ | $\lambda/10$ | $\lambda/40$ |
| 1 | 0 dB | +2.5 dB | +2.8 dB |
| 2 | −1.4 dB | +2.5 dB | +3.2 dB |
| 10 | −2 dB | +2.5 dB | +6.8 dB |

The results show that sinc function interpolation will expand an effect of noise to more points than linear interpolation since sinc function interpolation uses adjacent four data points while linear interpolation uses only adjacent two data points. Thus, the results show that linear interpolation is superior to sinc function interpolation as an interpolation method for data obtained by sufficiently dense sampling with respect to the frequency component of the signal.

Figure 10:
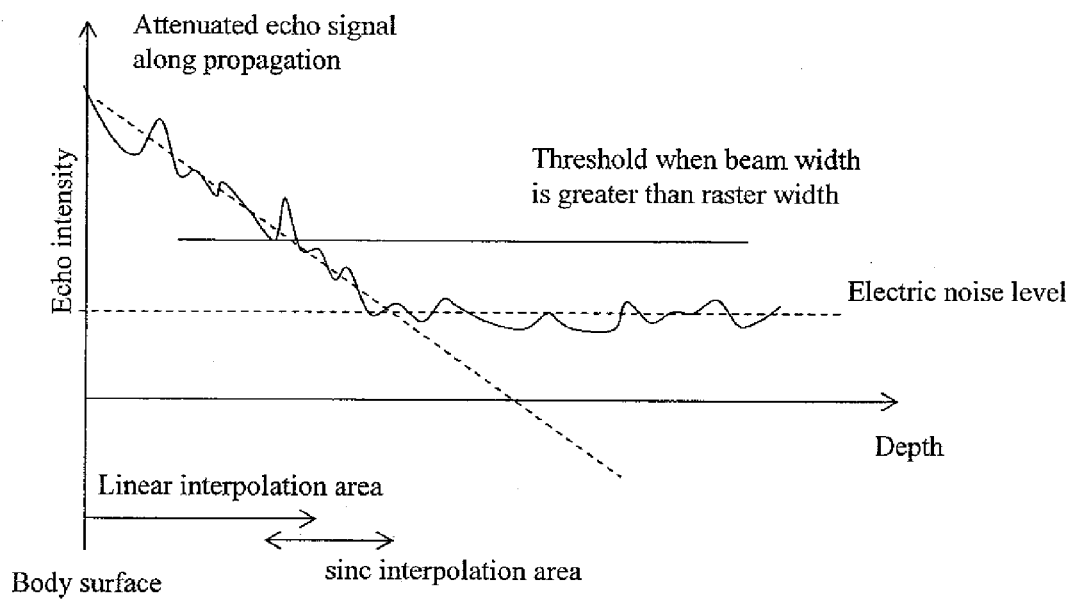
FIG. 10 illustrates a signal dynamic range and how to switch an interpolation method.

The conclusion drawn from these results is that an adaptive transition of interpolation method for each signal as shown in FIG. 10 will be effective. Specifically, in this adaptive method, linear interpolation is applied to a signal having a wide effective beam width in a dynamic range while sinc function interpolation is applied to a signal having a narrow effective beam width in the dynamic range. Signal intensity and an electrical noise level specific to each device will not change much once a subject, and its site to be examined and a transmission focus point are determined. Thus, a transition depth can be preset for each mode.

Figure 11:
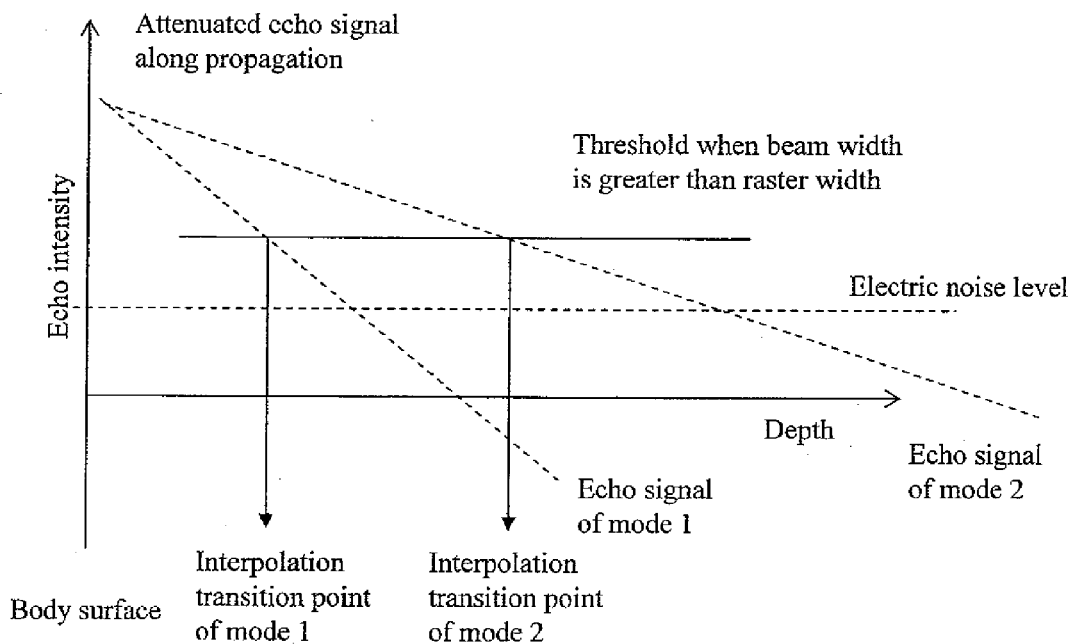
FIG. 11 illustrates that an attenuation rate varies depending on modes and an interpolation method transition point corresponds to each mode.

Typically, an imaging-target site is selected upon selection of ultrasonic probe connected to an ultrasonographic device. For example, in the case of a low-frequency probe for convex scanning, optimal imaging parameters are selected for each of target sites such as a liver, a kidney, an uterus, an embryo and an aorta. The selection and switching of a parameter set will be hereinbelow referred to as mode switching. The attenuation rate of an ultrasonic wave during propagation varies greatly depending on target sites described above. For example, if the target site is an embryo, most of the propagation medium is made of an amniotic fluid, and thus an ultrasonic wave from the site is little attenuated. On the other hand, if, for example, the target site is a liver, most of the propagation passage is substantially occupied by subcutaneous fat and the liver, which is an organ, so that the attenuation rate of an ultrasonic wave propagating through the passage is far higher than through an amniotic fluid. Hence, the slope of an echo signal relative to depth varies depending on modes as shown in FIG. 11. Thus, the depth where a beam width is greater than a raster width in the dynamic range also varies depending on modes. Note that the attenuation rate of an ultrasonic wave from an imaging-target site also varies depending on the type and extent of disease (if the target site is a cirrhotic liver, for example). Thus, the ultrasonographic device should preferably allow fine mode adjustment applicable to various conditions including lesions and extents of disease.

Figure 12:
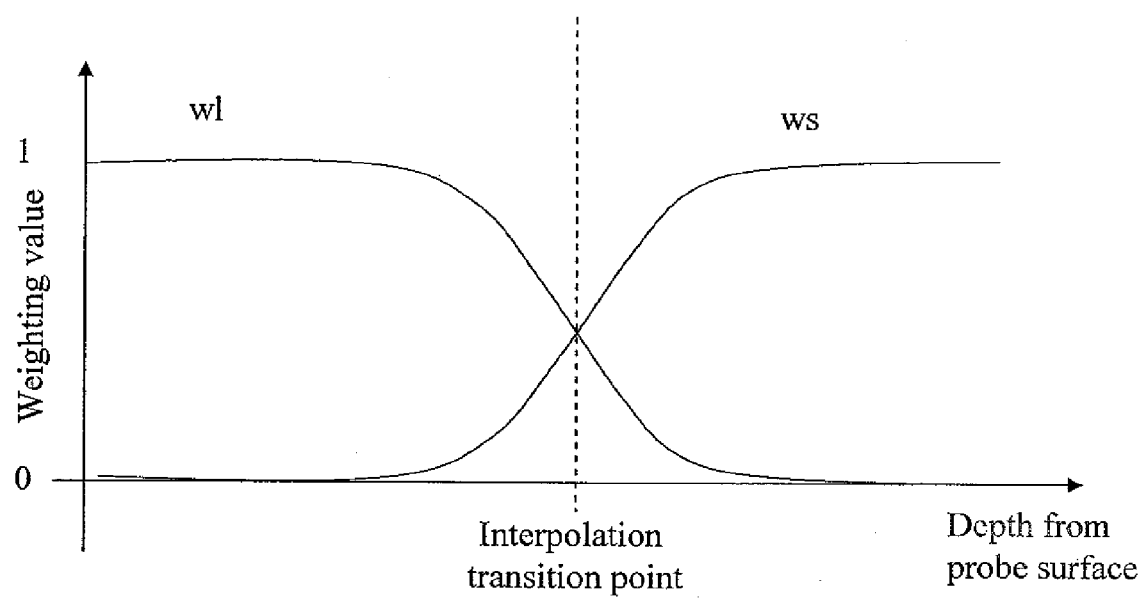
FIG. 12 illustrates changes in weighting functions for interpolation method transition.

In the light of these circumstances, an ultrasonographic device according to one of the embodiments includes a depth storage unit 21, and previously stores, in the depth storage unit 21, data on interpolation method transition depths, that is, data on depths for switching between linear interpolation and sinc function interpolation. The interpolation processor 30 refers to the interpolation method transition depth data stored in the depth storage unit 21. Then, the interpolation processor 30 interpolates a data point by the linear interpolation method when the data point has a depth less than the stored interpolation method transition depth for the employed mode, but interpolates the data point by the sinc function interpolation method when the data point has a depth more than this stored interpolation method transition depth. Here, if the interpolation method is switched at a switching depth in a manner of steeply transitioning from linear interpolation to sinc function interpolation, the transition point might appear as an artifact. This is prevented by a method using continuously varying weighting values to be described below. Specifically, assume that a linear-interpolated value is Il, a weighting value for Il is wl, a sinc-function-interpolated value is Is, and a weighting value for Is is ws. Then, an output I of an interpolation result using these weighting values wl and ws is expressed by the following expression. The ultrasonographic device may be configured to allow the weighting value for use to continuously transition between wl and ws about a transition point as show in FIG. 12.

$$I = wl \times Il + ws \times Is$$

Figure 13:
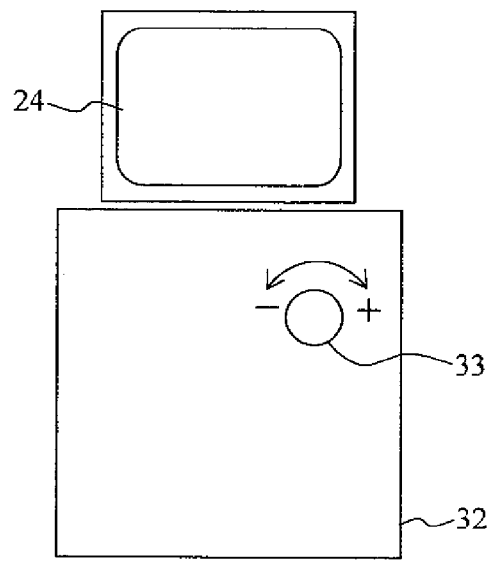
FIG. 13 is a schematic diagram of an interface of transition point control.
Figure 14:
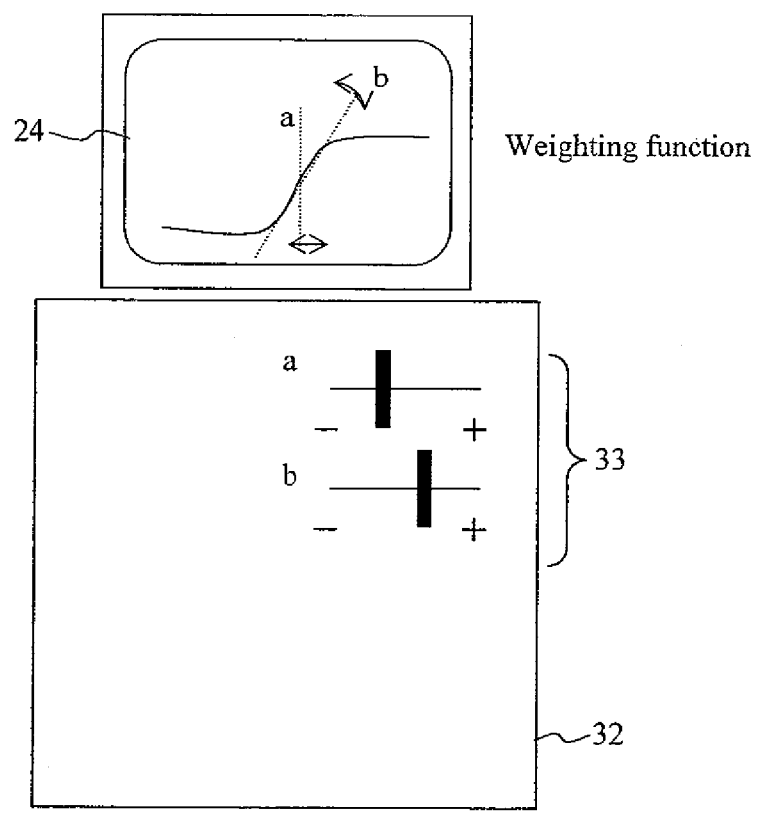
FIG. 14 is a schematic diagram of another interface of transition point control.

Note that, an interface of transition point control 33 may be provided in a control panel of a diagnostic system 32 so as to allow an operator to control the position of this transition point as he/she likes. In this case, the ultrasonographic device may allow the operator either to move the transition point in the depth direction or to change the aforementioned ratio of wl to ws. FIG. 13 shows an ultrasonographic device allowing an operator to set a transition point by inputting a single parameter indicating a position in the depth direction, while FIG. 14 shows an ultrasonographic device allowing an operator to set conditions for changing the wl-to-ws ratio by inputting two parameters of a transition point (indicated by "a" in FIG. 14) and a slope of changing the wl-to-ws ratio during the transition (indicated by "b" in FIG. 14).

In the device shown in FIG. 1, the position of the interpolation transition point is fixed once an imaging mode is determined. However, actually, the optimal position of the transition point for a certain imaging-target site varies greatly depending on variation among subjects to be examined. For example, if the imaging-target site is a lever, the optimal transition position greatly depends on conditions including an extent of disease progress such as cirrhosis, and a subcutaneous fat thickness. Thus, the optimal position of the transition point should preferably be set for each obtained signal. In particular, an ultrasonographic device has a function called a time gain control, and thus is capable of adjusting a gain on the signal depth basis. Hence, a signal width in the dynamic range is not always completely determined by parameters (such as a target site, a focus point of transmission beam and a transmit/receive frequency) for determining an imaging mode of the device.

Figure 15:
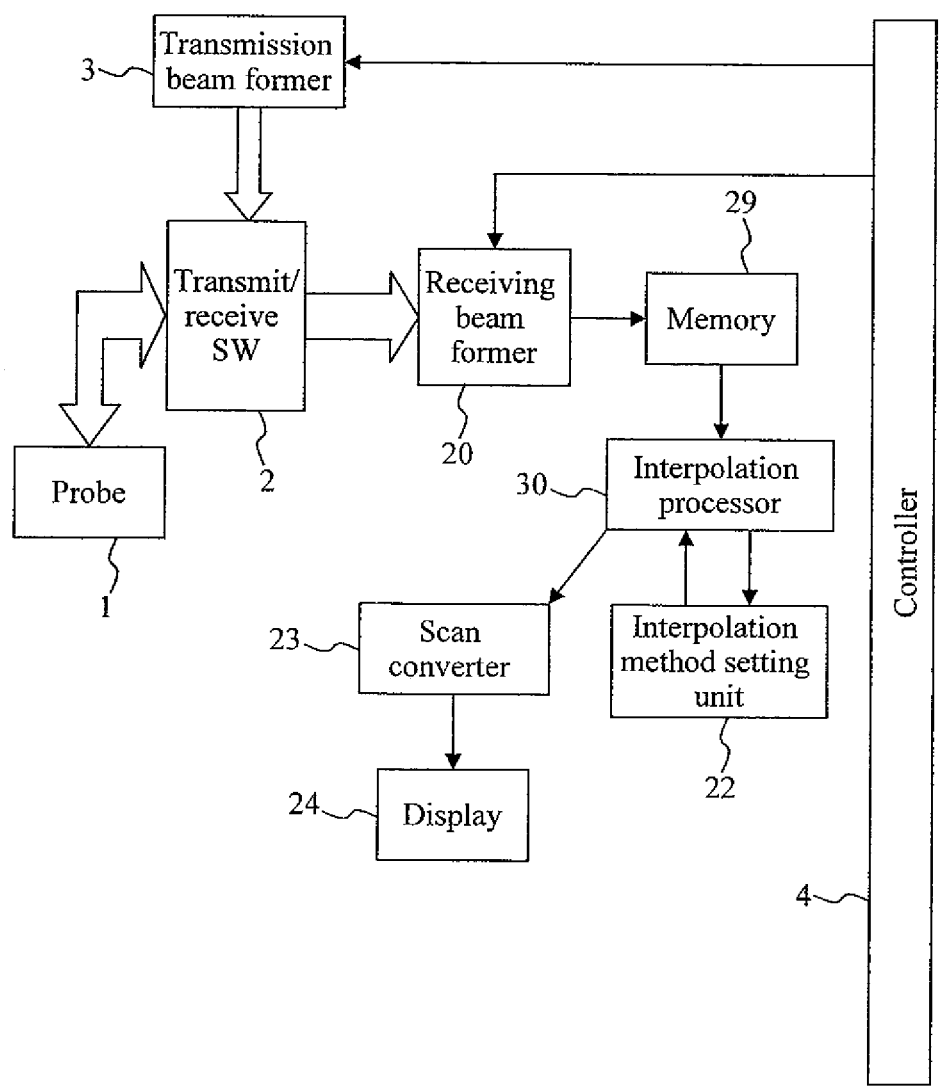
FIG. 15 is a functional block diagram illustrating another example of the ultrasonographic device according to the present invention.

FIG. 15 shows a configuration example of the device applicable to this case. The device of this embodiment is the same as the device shown in FIG. 1 except that this device including an interpolation method setting unit 22, and thus description for the same parts as the foregoing device will be omitted. Upon receipt of an input of interpolation-target one-dimensional data obtained along a raster, the interpolation method setting unit 22 computes a signal intensity change profile in the depth direction as shown in FIG. 10. Then, based on the change profile, the interpolation method setting unit 22 obtains a point at which the signal intensity goes below the preset dynamic range. This point will be hereinbelow referred to as interpolation transition point. In FIG. 10, the solid line indicates an actual data while the dotted line indicates data on a computed trend of the actual data in the depth direction. This trend may be computed by applying a filter such as a low-pass filter or a median filter on data indicated by the solid line. Alternatively, the trend may be computed by assuming that an echo intensity I(x) at a depth x is expressed by I(x)=ax+b, and obtaining the coefficients a and b by least-square fitting.

If the interpolation method transition point varies from one raster to another, artifacts appear in a stripe pattern in a resultant image. This may be prevented by such a method as obtaining a signal intensity change profile of an average data among multiple rasters or using an average value obtained by averaging the interpolation transition points computed for the respective rasters.

Figure 16:
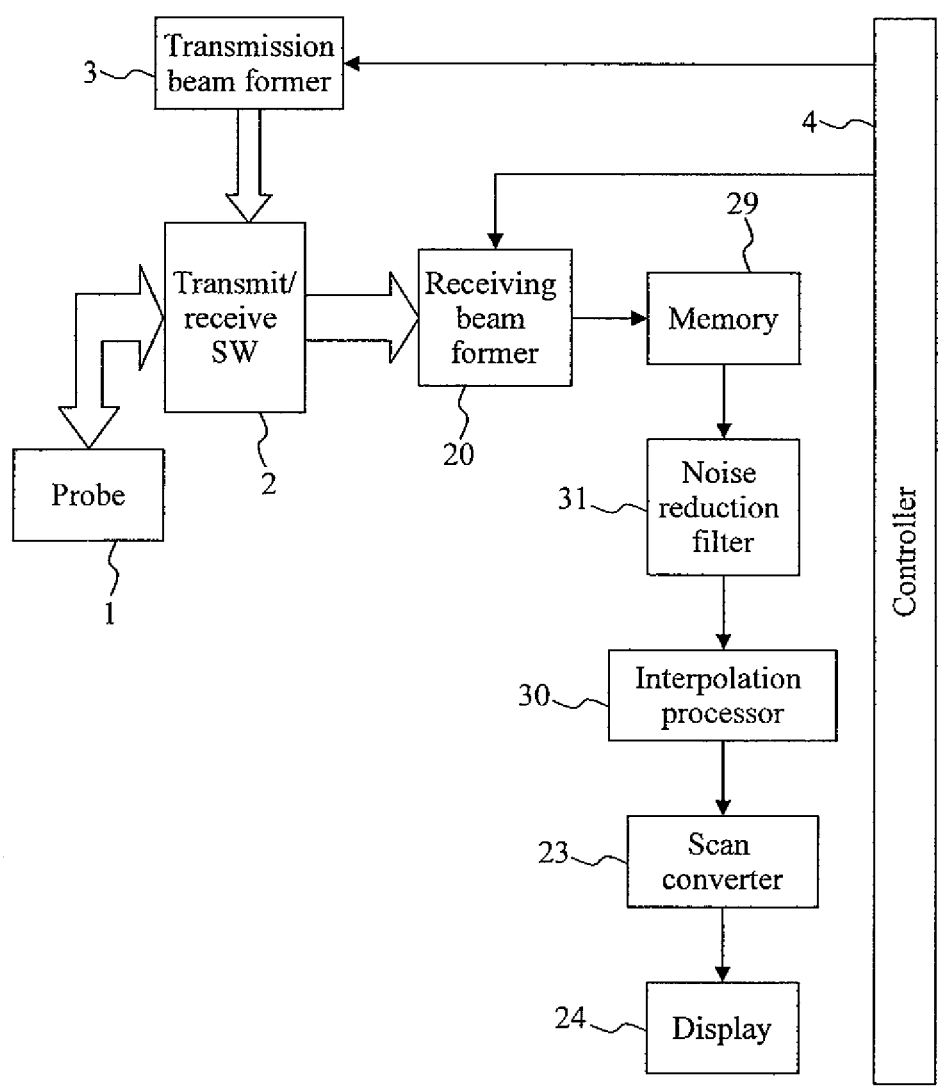
FIG. 16 is a functional block diagram illustrating still another example of the ultrasonographic device according to the present invention.

As another embodiment, FIG. 16 shows a configuration example of the device applicable to the case where data is interpolated after improving the S/N ratio thereof by using a signal processing technique. The specific processing performed by a noise reduction filter 31 shown in FIG. 16 will be described in detail with reference to FIGS. 17 to 19.

Figure 17:
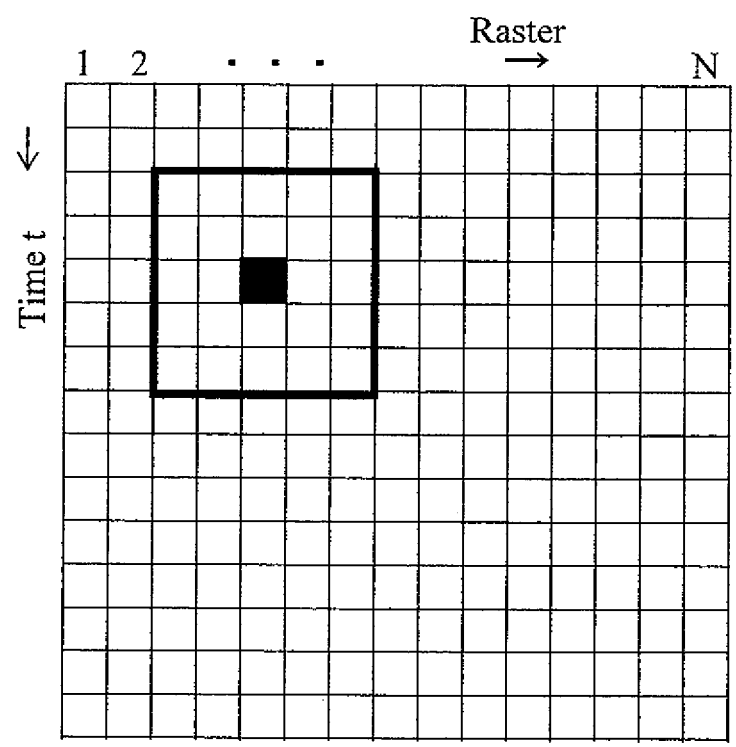
FIG. 17 illustrates a noise reduction filter.
Figure 17:
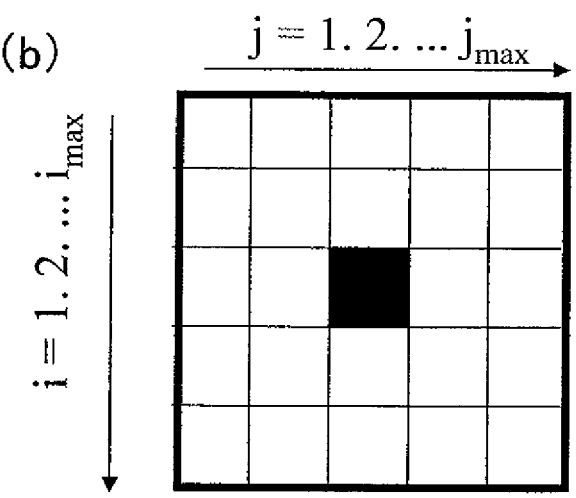
Figure 18:
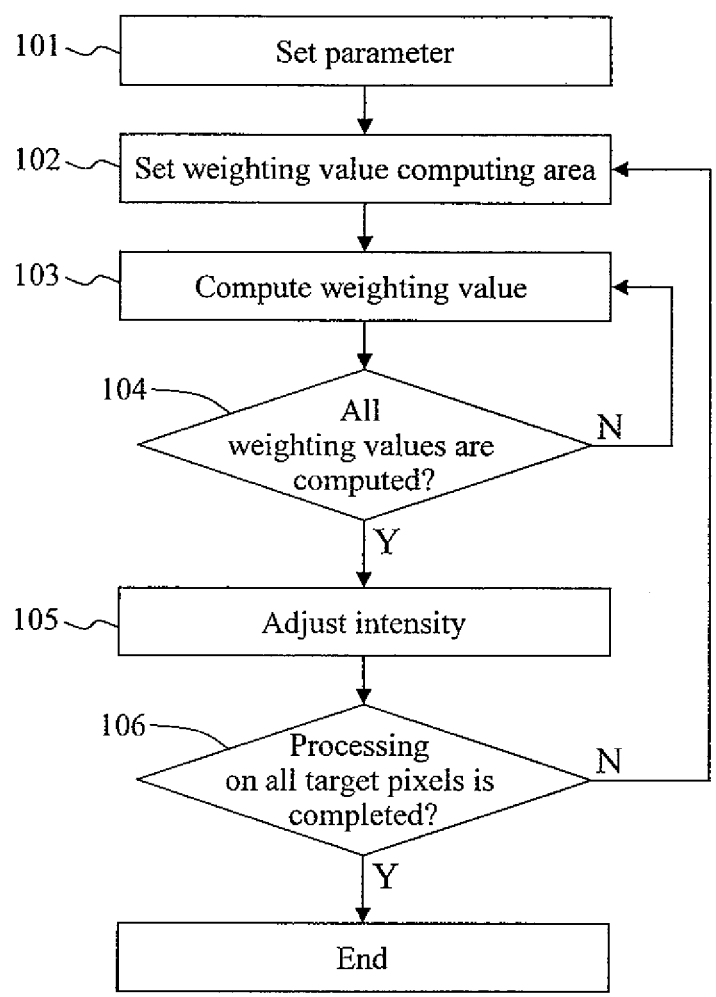
FIG. 18 is a flowchart for controlling the noise reduction filter.

FIG. 17 illustrates a target pixel for noise reduction processing and an area used for computing weighting values for the pixel. FIG. 18 is a flowchart of the noise reduction processing.

A memory in the noise reduction filter 31 stores therein two-dimensional data formed of N one-dimensional image data sets each changing in the direction of the time axis t as shown in FIG. 17. Specifically, these one-dimensional image data sets respectively correspond to 1st, 2nd, . . . , N-th rasters and are arranged side by side in the direction where the rasters are arranged.

Firstly, an area (weighting value computing area) surrounding the target pixel to be used for computing weighting values for a noise-reduction processing target pixel (intensity $I_0$) are set. The weighting value computing area includes pixels ($i_{max} \times j_{max}$ pixels each having an intensity $I_{ij}$) surrounding the target pixel, where i=1, 2, . . . , $i_{max}$ and j=1, 2, . . . , $j_{max}$. The larger the weighting value computing area, the more effective the obtained noise reduction filter is but the lower the required computation speed is. The values of $i_{max}$ and $j_{max}$ and a shape of a weighting function are set through a parameters set process 101 shown in FIG. 18. In the parameters set process 101, a difference between the intensity $I_0$ of the target pixel and the intensity $I_{ij}$ of each pixel in the weighting value computing area surrounding the target pixel is computed. This computation is performed on each target pixel of this processing. Then, a histogram of the computed differences of intensity is created, and a width of the histogram is computed. This width of the histogram of the differences of intensity is used for setting a weighting function to be described later.

Then, in a weighting value computing area setting process 102, set are pixels in the weighting value computing area, which is defined by the position of the target pixel and the values of $i_{max}$ and $j_{max}$. In a weighting value computing process 103, weighting values are computed by using weighting functions to be described later. If it is decided that this process has been performed on all the pixels in the weighting value computing area in a weighting value computation completion decision process 104, an intensity value to be assigned to the target pixel in the foregoing process of setting computing area is computed in an intensity adjustment process 105. If, in a target pixel completion decision process 106, it is decided that the target pixel position has been shifted in the foregoing process of setting computing area till the intensity values are computed for all the pixels in a two-dimensional data for extracting a structure of a body tissue, the noise reduction processing is completed.

Figure 19:
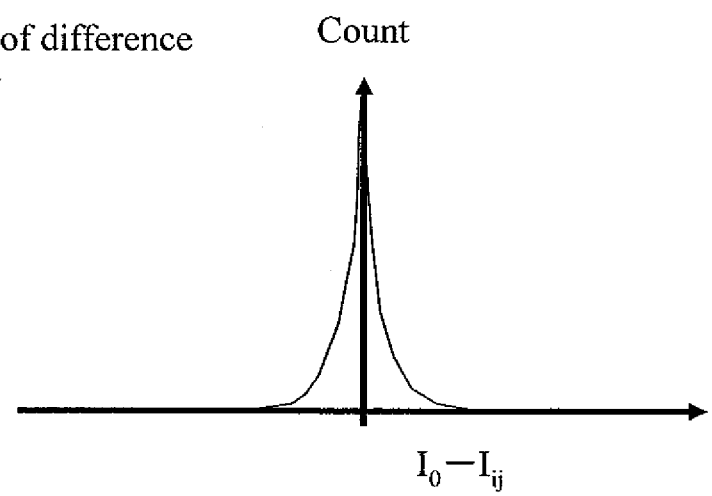
FIG. 19 illustrates a weighting function after application of the noise reduction filter.
Figure 19:
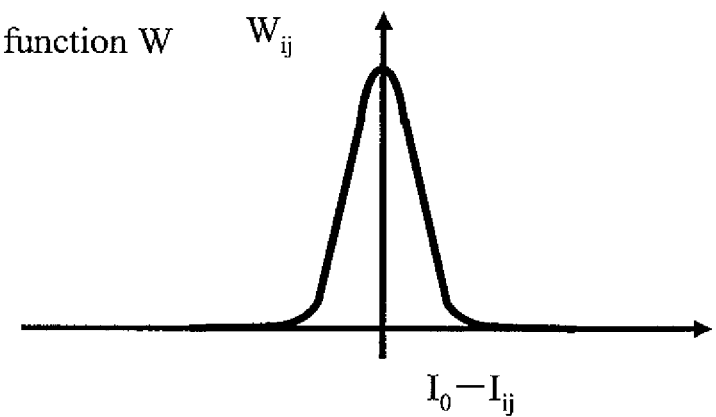

FIG. 19 illustrates the aforementioned weighting function. FIG. 19(a) shows the histogram of the aforementioned differences of intensity obtained from a typical ultrasonic image. In FIG. 19(a), the horizontal axis indicates aforementioned difference of intensity ($I_0-I_{ij}$) while the vertical axis indicates appearance count of difference of intensity ($I_0-I_{ij}$). FIG. 19(b) shows an example of a weighting function W in which a weighting value decreases monotonically with the increase of the absolute value of difference of intensity ($I_0-I_{ij}$). A weighting value $W_{ij}$ is computed for each value on the horizontal axis ($I_0-I_{ij}$). Examples of the weighting function W include not only an even-ordered polynomial but also various even functions such as Gaussian function and the function of $1/(x^2+a^2)$. The function W takes a local maximum point with ($I_0-I_{ij}$)=0, and the integration value of the absolute value W of the function from the negative infinity to the positive infinity is finite. Based on the weighting function, the intensity value of the target pixel is computed by the following expression:

$$I_0+\Sigma\{(I_{ij}-I_0)W_{ij}\}/\Sigma W_{ij}.$$

This noise reduction filter functions differently depending on the intensity continuity from the target pixel to the surrounding pixels. The noise reduction filter functions as a two-dimensional low-pass filter, when the difference between the intensity $I_0$ and the intensity $I_{ij}$ of each surrounding pixel is small. This is because a substantially constant weighting value is assigned to the target pixel in this case. On the other hand, the noise reduction filter functions as a one-dimensional low-pass filter and an all-pass filter, when the pixel having the intensity $I_0$ is positioned at an interface between two structures (tissues). Specifically, the noise reduction filter functions as a one-dimensional low-pass filter in the direction parallel to the interface between the two structures, since a high weighting value is assigned to each pixel positioned on the interface. Meanwhile, the noise reduction filter functions as an all-pass filter in the direction perpendicular to the interface between the two structures. Accordingly, the noise reduction filter will never dampen sharpness at an interface. As described above, the ultrasonographic device according to this embodiment employs a nonlinear filter that functions differently depending on the intensity distribution profile of the pixels. This allows the ultrasonographic device to perform noise reduction processing while minimizing an effect of dampening edges in an image, and thus enlarges an effective dynamic range for each signal. Thereby, the ultrasonographic device can shift the transition point from linear interpolation to sinc function interpolation to a deeper part.

INDUSTRIAL APPLICABILITY

The present invention makes it possible to provide an ultrasonogram having a preferable spatial resolution and signal/noise ratio.

The invention claimed is:

1. An ultrasonographic device comprising:
    an ultrasonic probe configured to transmit an ultrasonic beam to an object and receive an ultrasonic echo signal;
    a transmission beam former configured to transmit a signal to the ultrasonic probe so as to cause the ultrasonic probe to emit the ultrasonic beam for scanning a sectoral region;
    a receiving beam former configured to receive echo signals from a plurality of data points on rasters in the sectoral region scanned by the ultrasonic probe;
    a memory configured to store therein, the echo signals from the plurality of data points as data sets for displaying an ultrasonogram;
    an interpolation processor configured to interpolate a data set between each adjacent two rasters in the data sets stored in the memory, where the interpolation processor interpolates the data set by using a plurality of interpolation methods used for differing depths measured with respect to a surface of the object, respectively, wherein the plurality of interpolation methods include linear interpolation applied in interpolating data sets positioned closer to the surface of the object than a switching depth, and sinc function interpolation applied in interpolating data sets positioned farther away from the surface of the object than the switching depth; and an inputter configured to receive an input of the switching depth representing a preset interpolation method transition depth set with respect to the surface of the object, where switching transition between the plurality of interpolation methods is performed.

2. The ultrasonographic device according to claim 1, wherein the plurality of interpolation methods include two-or-more dimensional function interpolation.

3. The ultrasonographic device according to claim 2, wherein an interpolated data set is computed as a weighted sum of a first data set interpolated by the linear interpolation and a second data set interpolated by the two-or-more dimensional function interpolation, and in this computation, when a data point depth is closer to the object surface than the preset interpolation method transition depth, an increased weighting value is assigned to the first data set interpolated by the linear interpolation, and when the data point depth is farther from the object surface than the preset interpolation method transition depth, an increased weighting value is assigned to the second data set interpolated by the two-or-more dimensional function interpolation.

4. The ultrasonographic device according to claim 1, wherein the ultrasonographic device performs noise reduction before interpolating the data set.

5. The ultrasonographic device according to claim 1, wherein the ultrasonographic device stores a plurality of switching depths representing a plurality of preset interpolation transition depths, where switching transition between the plurality of interpolation methods is performed.

6. An ultrasonographic device comprising:

an ultrasonic probe that transmits an ultrasonic beam to an object and receives an ultrasonic echo signal;

a transmission beam former which transmits a signal to the ultrasonic probe so as to cause the ultrasonic probe to emit the ultrasonic beam for scanning a sectoral region;

a receiving beam former which receives echo signals from a plurality of data points on rasters in the sectoral region scanned by the ultrasonic probe;

a memory which stores therein the echo signals from the plurality of data points as data sets for displaying an ultrasonogram;

an interpolation method setter configured to compute a signal intensity change profile of each echo signal in the depth direction of the object along the corresponding raster, and which sets, as a preset interpolation method transition depth, a depth point measured from a surface of the object, at which the signal intensity goes below a preset signal intensity level; and an interpolation processor which interpolates a data set between each adjacent two rasters in the data sets stored in the memory, by interpolating data points positioned closer to the surface of the object than the preset interpolation method transition depth by linear interpolation, and by interpolating data points positioned farther away from the surface of the object than the preset interpolation method transition depth by a sinc function interpolation.

7. The ultrasonographic device according to claim 6, wherein the interpolated data set is computed as a weighted sum of a first data set interpolated by the linear interpolation and a second data set interpolated by the sinc function interpolation, and in this computation, when a data point depth is closer to the surface of the object than the preset interpolation method transition depth, an increased weighting value is assigned to the first data set interpolated by the linear interpolation, and when the data point depth is farther from the surface of the object than the preset interpolation method transition depth, an increased weighting value is assigned to the second data set interpolated by the sinc function interpolation.

8. The ultrasonographic device according to claim 6, wherein further comprising:

a weighter unit configured to assign weighting values respectively to the first data set interpolated by the linear interpolation and the second data set interpolated by the sinc function interpolation, and combining the weighted data sets; and an inputter configured to receive a control of the weighting values.

9. The ultrasonographic device according to claim 6, further comprising:

a depth storage configured to store transition depth data, and wherein the interpolation processor references the transition depth data to determine which interpolation method to use for a given depth as measured from the surface of the object.

10. The ultrasonographic device according to claim 1, further comprising:

a depth storage configured to store transition depth data, and wherein the interpolation processor references the transition depth data to determine which interpolation method to use for a given depth, to interpolate the data set.

11. The ultrasonographic device according to claim 1, wherein an interpolated data set is computed as a weighted sum of a first data set interpolated by the linear interpolation and a second data set interpolated by the sinc function interpolation, and in this computation, when a data point depth closer to the surface of the object than the preset interpolation method transition depth, an increased weighting value is assigned to the first data set interpolated by the linear interpolation, and when the data point depth farther from the surface of the object than the preset interpolation method transition depth, an increased weighting value is assigned to the second data set interpolated by the sinc function interpolation.

* * * * *